(12) United States Patent
Ransbury et al.

(10) Patent No.: US 9,884,182 B2
(45) Date of Patent: Feb. 6, 2018

(54) CATHETER SYSTEM FOR ACUTE NEUROMODULATION

(71) Applicant: Interventional Autonomics Corporation, Chapel Hill, NC (US)

(72) Inventors: Terrance J Ransbury, Chapel Hill, NC (US); Richard S Stack, Chapel Hill, NC (US); William E Sanders, Chapel Hill, NC (US); Stephen C Masson, Raleigh, NC (US)

(73) Assignee: INTERVENTIONAL AUTONOMICS CORPORATION, Chapel Hill, NC (US)

( * ) Notice: Subject to any disclaimer, the term of this patent is extended or adjusted under 35 U.S.C. 154(b) by 104 days.

(21) Appl. No.: 14/151,755

(22) Filed: Jan. 9, 2014

(65) Prior Publication Data

US 2014/0128750 A1      May 8, 2014

Related U.S. Application Data

(63) Continuation of application No. PCT/US2012/046332, filed on Jul. 11, 2012.
(Continued)

(51) Int. Cl.
*A61N 1/00* (2006.01)
*A61N 1/05* (2006.01)
(Continued)

(52) U.S. Cl.
CPC ............ *A61N 1/056* (2013.01); *A61B 5/0215* (2013.01); *A61N 1/3605* (2013.01); *A61N 1/36114* (2013.01); *A61N 1/36564* (2013.01)

(58) Field of Classification Search
USPC ......................................................... 607/116
See application file for complete search history.

(56) References Cited

U.S. PATENT DOCUMENTS

| 4,240,433 A | 12/1980 | Bordow |
| 5,154,172 A | 10/1992 | Terry, Jr. |

(Continued)

FOREIGN PATENT DOCUMENTS

| WO | WO 2005/065771 A1 | 7/2005 |
| WO | WO 2007/075593 A1 | 7/2007 |

(Continued)

OTHER PUBLICATIONS

Supplementary European Search Report for European Application No. 12821988.8, corresponding to PCT/US2012/046332.
(Continued)

*Primary Examiner* — Nicole F Lavert

(57) ABSTRACT

A neuromodulation system includes a first therapy element adapted for positioning within a superior vena cava, and a second therapy element adapted for positioning within a pulmonary artery. The first therapy element is carried on a first elongate flexible shaft, and the second therapy element is carried on a second elongate flexible shaft. One of the first and second shafts is slidably received within a lumen of the other of the first and second shafts—so that the second therapy element may be advanced within the body relative to the first therapy element. A stimulator is configured to energize the first therapy element within the first blood vessel to deliver therapy to a first nerve fiber disposed external to the superior vena cava and to energize the second therapy element within the pulmonary artery to deliver sympathetic therapy to a second nerve fiber disposed external to the pulmonary artery. For treatment of heart failure, the first nerve fiber may be a vagus nerve and the second nerve fiber may be a sympathetic nerve fiber.

6 Claims, 4 Drawing Sheets

Related U.S. Application Data

(60) Provisional application No. 61/506,164, filed on Jul. 11, 2011.

(51) Int. Cl.
   *A61N 1/36* (2006.01)
   *A61B 5/0215* (2006.01)
   *A61N 1/365* (2006.01)

(56) References Cited

U.S. PATENT DOCUMENTS

| | | |
|---|---|---|
| 5,179,950 A | 1/1993 | Stanislaw |
| 5,269,303 A | 12/1993 | Wernicke |
| 5,304,206 A | 4/1994 | Baker, Jr. |
| 5,531,779 A | 7/1996 | Dahl |
| 5,628,779 A | 5/1997 | Bornzin et al. |
| 5,651,378 A | 7/1997 | Matheny |
| 5,700,282 A | 12/1997 | Zabara |
| 5,707,400 A | 1/1998 | Terry, Jr. |
| 5,913,876 A | 6/1999 | Taylor |
| 5,928,272 A | 7/1999 | Adkins |
| 5,954,761 A | 9/1999 | Machek |
| 6,181,966 B1 | 1/2001 | Nigam |
| 6,292,695 B1 | 9/2001 | Webster, Jr. |
| 6,429,217 B1 | 8/2002 | Pkas |
| 6,445,953 B1 | 9/2002 | Bulkes |
| 6,449,507 B1 | 9/2002 | Hill |
| 6,473,644 B1 | 10/2002 | Terry, Jr. |
| 6,479,523 B1 | 11/2002 | Pkas |
| 6,522,926 B1 | 2/2003 | Kieval |
| 6,529,779 B1 | 3/2003 | Sutton |
| 6,542,774 B2 | 4/2003 | Hill |
| 6,564,096 B2 | 5/2003 | Mest |
| 6,616,624 B1 | 9/2003 | Kieval |
| 6,622,041 B2 | 9/2003 | Terry, Jr. |
| 6,656,960 B2 | 12/2003 | Pkas |
| 6,690,971 B2 | 2/2004 | Schauerte |
| 6,697,676 B2 | 2/2004 | Dahl |
| 6,721,603 B2 | 4/2004 | Zabara |
| 6,748,272 B2 | 6/2004 | Carlson |
| 6,778,854 B2 | 8/2004 | Pkas |
| RE38,705 E | 2/2005 | Hill |
| 6,850,801 B2 | 2/2005 | Kieval |
| 6,885,888 B2 | 4/2005 | Rezai |
| 6,907,285 B2 | 6/2005 | Denker |
| 6,912,419 B2 | 6/2005 | Hill |
| 6,934,583 B2 | 8/2005 | Weinberg |
| 6,937,896 B1 | 8/2005 | Kroll |
| 6,978,174 B2 | 12/2005 | Gelfand |
| 6,985,774 B2 | 1/2006 | Kieval |
| 7,069,070 B2 | 6/2006 | Carlson |
| 7,072,720 B2 | 7/2006 | Pkas |
| 7,110,828 B2 | 9/2006 | Kolberg |
| 7,123,959 B2 | 10/2006 | Cates |
| 7,123,961 B1 | 10/2006 | Kroll |
| 7,139,607 B1 | 11/2006 | Shelchuk |
| 7,142,917 B2 | 11/2006 | Fukui |
| 7,149,574 B2 | 12/2006 | Yun |
| 7,162,303 B2 | 1/2007 | Levin |
| 7,181,288 B1 | 2/2007 | Rezai |
| 7,184,829 B2 | 2/2007 | Hill |
| 7,194,313 B2 | 3/2007 | Libbus |
| 7,225,019 B2 | 5/2007 | Jahns |
| 7,231,260 B2 | 6/2007 | Wallace |
| 7,269,457 B2 | 9/2007 | Shafer |
| 7,277,761 B2 | 10/2007 | Shelchuk |
| 7,299,091 B2 | 11/2007 | Barrett |
| 7,310,552 B2 | 12/2007 | Pkas |
| 7,330,765 B2 | 2/2008 | Haldeman |
| 7,336,997 B2 | 2/2008 | Fukui |
| 7,340,299 B2 | 3/2008 | Pkas |
| 7,363,076 B2 | 4/2008 | Yun |
| 7,386,345 B2 | 6/2008 | Pastore |
| 7,455,753 B2 | 11/2008 | Roth |
| 7,477,945 B2 | 1/2009 | Rezai |
| 7,485,104 B2 | 2/2009 | Kieval |
| 7,486,991 B2 | 2/2009 | Libbus |
| 7,499,744 B2 | 3/2009 | Carlson |
| 7,499,748 B2 | 3/2009 | Moffitt |
| 7,509,166 B2 | 3/2009 | Libbus |
| 7,519,421 B2 | 4/2009 | Denker |
| 7,519,424 B2 | 4/2009 | Dennis |
| 7,532,938 B2 | 5/2009 | Machado |
| 7,555,341 B2 | 6/2009 | Moffitt |
| 7,555,351 B2 | 6/2009 | Zhang |
| 7,561,923 B2 | 7/2009 | Libbus |
| 7,572,226 B2 | 8/2009 | Scheiner |
| 7,596,413 B2 | 9/2009 | Libbus |
| 7,617,003 B2 | 11/2009 | Caparso |
| 7,617,005 B2 | 11/2009 | Demarais |
| 7,620,451 B2 | 11/2009 | Demarais |
| 7,634,317 B2 | 12/2009 | Ben-David |
| 7,643,875 B2 | 1/2010 | Heil, Jr. |
| 7,647,114 B2 | 1/2010 | Libbus |
| 7,647,115 B2 | 1/2010 | Levin |
| 7,653,438 B2 | 1/2010 | Deem |
| 7,676,275 B1 | 3/2010 | Farazi |
| 7,717,948 B2 | 5/2010 | Demarais |
| 7,747,323 B2 | 6/2010 | Libbus |
| 7,756,583 B2 | 7/2010 | Demarais |
| 7,765,000 B2 | 7/2010 | Zhang |
| 7,769,446 B2 | 8/2010 | Moffitt |
| 7,769,470 B1 | 8/2010 | Rezai |
| 7,778,704 B2 | 8/2010 | Rezai |
| 7,778,711 B2 | 8/2010 | Ben-David |
| 7,783,362 B2 | 8/2010 | Whitehurst |
| 7,801,627 B2 | 9/2010 | Haldeman |
| 7,809,447 B2 | 10/2010 | Dreier |
| 7,813,812 B2 | 10/2010 | Kieval |
| 7,833,164 B2 | 11/2010 | Scheiner |
| 7,840,278 B1 | 11/2010 | Pkas |
| 7,853,333 B2 | 12/2010 | Demarais |
| 7,865,237 B2 | 1/2011 | Machado |
| 7,865,249 B2 | 1/2011 | Reddy |
| 7,869,881 B2 | 1/2011 | Libbus |
| 7,873,417 B2 | 1/2011 | Demarais |
| 7,877,146 B2 | 1/2011 | Rezai |
| 7,881,788 B2 | 2/2011 | Fukui |
| 7,885,711 B2 | 2/2011 | Ben-Ezra |
| 7,890,187 B2 | 2/2011 | Hochareon |
| 7,890,188 B2 | 2/2011 | Zhang |
| 7,904,175 B2 | 3/2011 | Scott |
| 7,917,230 B2 | 3/2011 | Bly |
| 7,937,143 B2 | 5/2011 | Demarais |
| 7,949,409 B2 | 5/2011 | Bly |
| 7,962,214 B2 | 6/2011 | Byerman |
| 8,024,050 B2 | 9/2011 | Libbus |
| 8,032,215 B2 | 10/2011 | Libbus |
| 8,046,075 B2 | 10/2011 | Rezai |
| 8,126,560 B2 | 2/2012 | Scheiner |
| 8,412,350 B2 | 4/2013 | Bly |
| 2002/0120304 A1 | 8/2002 | Mest |
| 2003/0004549 A1 | 1/2003 | Hill |
| 2003/0229380 A1 | 12/2003 | Adams |
| 2004/0019364 A1 | 1/2004 | Kieval |
| 2004/0176672 A1 | 9/2004 | Silver |
| 2005/0096710 A1 | 5/2005 | Kieval |
| 2005/0149156 A1 | 7/2005 | Libbus |
| 2005/0251238 A1 | 11/2005 | Wallace |
| 2005/0251239 A1 | 11/2005 | Wallace |
| 2005/0288730 A1 | 12/2005 | Deem et al. |
| 2006/0079945 A1 | 4/2006 | Libbus |
| 2006/0229677 A1 | 10/2006 | Moffitt |
| 2006/0235474 A1 | 10/2006 | Demarais |
| 2006/0253161 A1 | 11/2006 | Libbus |
| 2007/0129763 A1 | 6/2007 | Cates |
| 2007/0142879 A1 | 6/2007 | Greenberg |
| 2007/0191904 A1 | 8/2007 | Libbus |
| 2007/0282412 A1 | 12/2007 | Soltis |
| 2007/0282414 A1 | 12/2007 | Soltis |
| 2007/0288076 A1 | 12/2007 | Bulkes |
| 2007/0293925 A1 | 12/2007 | Zarembo |
| 2008/0009917 A1 | 1/2008 | Rossing |
| 2008/0183259 A1 | 7/2008 | Bly |

(56) References Cited

U.S. PATENT DOCUMENTS

| | | |
|---|---|---|
| 2008/0183264 A1 | 7/2008 | Bly |
| 2008/0234779 A1 | 9/2008 | Pedersen |
| 2008/0288017 A1 | 11/2008 | Kieval |
| 2008/0312712 A1 | 12/2008 | Penner |
| 2009/0005859 A1 | 1/2009 | Keilman |
| 2009/0030331 A1 | 1/2009 | Hochareon et al. |
| 2009/0036940 A1 | 2/2009 | Wei |
| 2009/0155336 A1 | 6/2009 | Rezai |
| 2009/0171411 A1 | 7/2009 | Machado |
| 2009/0228078 A1 | 9/2009 | Zhang |
| 2009/0248119 A1 | 10/2009 | Libbus |
| 2009/0275997 A1 | 11/2009 | Faltys |
| 2009/0276025 A1 | 11/2009 | Burnes |
| 2009/0318989 A1 | 12/2009 | Tomaschko |
| 2010/0036451 A1 | 2/2010 | Hoffer |
| 2010/0100151 A1 | 4/2010 | Terry, Jr. |
| 2010/0113890 A1 | 5/2010 | Cho |
| 2010/0114254 A1 | 5/2010 | Kornet |
| 2010/0137949 A1 | 6/2010 | Mazgalev |
| 2010/0191304 A1 | 7/2010 | Scott |
| 2010/0204741 A1 | 8/2010 | Tweden |
| 2010/0222832 A1 | 9/2010 | Zhang |
| 2011/0029037 A1 | 2/2011 | Rezai |
| 2011/0098762 A1 | 4/2011 | Rezai |
| 2011/0152877 A1 | 6/2011 | Bly |
| 2011/0152974 A1 | 6/2011 | Rezai |

FOREIGN PATENT DOCUMENTS

| | | | |
|---|---|---|---|
| WO | WO 2007/092330 | * 8/2007 | ............... A61N 1/36 |
| WO | WO 2008/070189 A2 | 6/2008 | |
| WO | WO 2008/092246 A1 | 8/2008 | |
| WO | WO 2009/075750 A2 | 6/2009 | |
| WO | WO 2010/0174571 | 2/2010 | |
| WO | WO2012/149511 A2 | 11/2012 | |

OTHER PUBLICATIONS

Bilgutay et al, Vagal Tuning: a new concept in the treatment of supraventricular arrhythmias, angina pectoris, and heart failure, Journal of Thoracic of Cardiovascular Surgery, 1968, vol. 56, No. 1, 71-82.

Cooper et al, Neural effects on sinus rate and atrioventricular conduction produced by electrical stimulation from a transvenous electrode catheter in the canine right pulmonary artery, Circ. Res. 1980; 46; 48-57.

Koizumi et al, Function significance of coactivation of vagal and sympathetic cardiac nerves, Proc. Natl. Acad. Sci., USA, (1982)79: 2116-2120.

Bernston et al, Autonomic Determinism: The Modes of Autonomic Control, the Doctrine of Autonomic Space, and the Laws of Autonomic Constraint, Psychological Review, 1991, vol. 98, No. 4, 459-487.

Carlson et al, Selective Stimulation of Parasympathetic Nerve Fibers to the Human SA Node, Circulation, 1992: 85: 1311-1317.

Yang et al, Sequence of excitation as a factor in sympathetic-parasympathetic interactions in the heart, Circ. Res., 1992, 71: 898-905.

Thompson, Bradycardia Induced by Intravascular Versus Direct Stimulation of the Vagus Nerve, Ann Thorac. Surg, 1998, 65: 637-42.

Schuarte et al, Ventricular Rate Control During Atrial Fibrillation by Cardiac Parasympathetic Nerve Stimulation: A Transvenous Approach, Journal of the American College of Cardiology, vol. 34, No. 7 (Dec. 1999) p. 2043-50.

Schuarte et al, Catheter Stimulation of Cardiac Parasympathetic Nerves in Humans: A Novel Approach to the Cardiac ANS, Circulation 2001, 104: 2430-2435.

Kawashima et al, The autonomic nervous system of the human heart with special reference to its origin, course, and peripheral distribution, Anat Embryol, 2005, 209: 425-438.

Paton et al, The yin and yang of cardiac autonomic control: Vago-sympathetic interactions revisited, Brain Research Reviews, 2005, 49(3): 555-65.

Berntson et al, Cardiac autonomic balance versus cardiac regulatory capacity, Psychophysiology, 2008, 45: 643-652.

Olshansky, et al, Parasympathetic Nervous System and Heart Failure: Pathophysiology and Potential Implications for Therapy, Circulation 2008, 118: 863-871.

Meyer et al, Augmentation of Left Ventricular Contractility by Cardiac Sympathetic Neural Stimulation, Circ. Res., 2010, 121: 1286-1294.

Brown et al, Long term bradycardia by electrical pacing: a new method for studying heart rate reduction, Cardiovascular Research, 1994; 28: 1774-1779.

Goldberger et al, New technique for vagal nerve stimulation, Journal of Neuroscience Methods 91 (1999), 109-114.

Li et al, Vagal Nerve Stimulation Markedly Improves Long-Term Survival After Chronic Heart Failure in Rats, Circulation 2004; 109-120-124.

Schwartz et al, Long term vagal stimulation in patients with advanced heart failure. First experience in man., European Journal of Heart Failure 10(2008) 884-891.

Nabutovsky et al, Lead Design and Initial Applications of a New Lead for Long-Term Endovascular Vagal Stimulation, PACE, vol. 30, S215-S218. 2007.

Janes, Anatomy of Human Extrinsic Cardiac Nerves and Ganglia, Am. J. Cardiol 1986; 57:299-309.

Extended European Search Report for EP12777812.4.

PCT Search Report for PCT/US12/035712.

PCT Search Report for PCT/US12/046332, which corresponds to the present application.

File History for Related U.S. Appl. No. 13/547,031.

File History for Related U.S. Appl. No. 13/547,035.

File History for Related U.S. Appl. No. 14/064,544.

File History for Related U.S. Appl. No. 14/516,734.

PCT Search Report for PCT/US2012/046329.

European Examination Report for related European Application No. 12821988.8, corresponding to PCT/US2012/046332.

\* cited by examiner

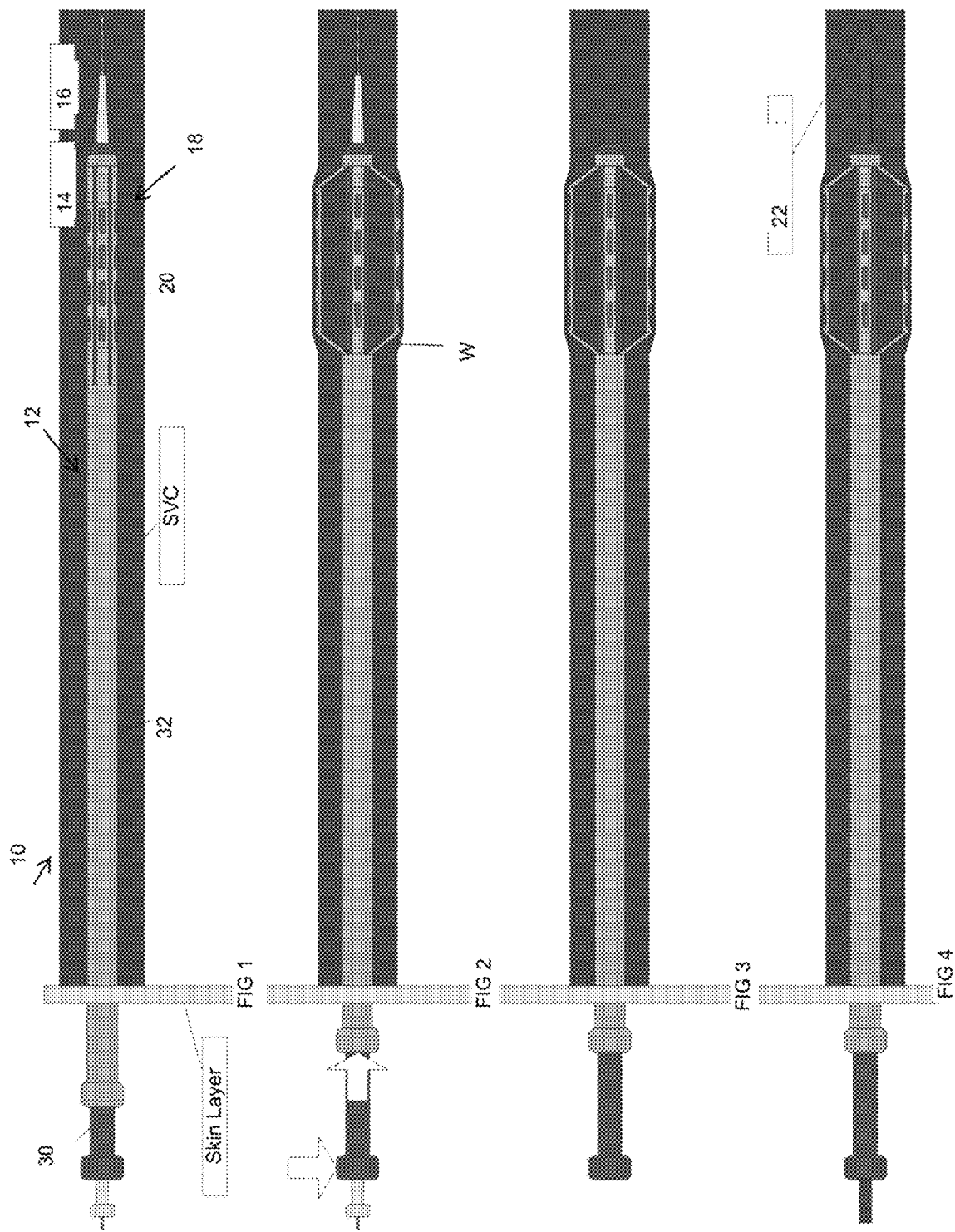

CATHETER SYSTEM FOR ACUTE NEUROMODULATION

Priority: This application is a continuation of co-pending application PCT/US2012/46332 filed 11 Jul. 2012, which claims the benefit of U.S. Provisional Application No. 61/506,164, filed 11 Jul. 2011, each of which is incorporated herein by reference.

TECHNICAL FIELD OF THE INVENTION

The present application generally relates to systems and methods for acute neuromodulation using stimulation elements disposed within the vasculature.

BACKGROUND

Acute heart failure syndromes (AHFS) are serious conditions resulting in millions of hospitalizations each year. AHFS treatments can include pharmacologic inotrope administration—however side effects of such treatments, including arrhythmias and increased myocardial oxygen demand, can contribute to patient mortality. Additional treatments include administration of diuretics to treat pulmonary edema resulting from AHFS.

The autonomic nervous system includes the parasympathetic nervous system and the sympathetic nervous system. The parasympathetic and sympathetic nervous system have somewhat opposing effects on the cardiovascular system. One function of the parasympathetic nervous system is to slow the heart through action of the vagus nerve. On the other hand, the sympathetic nervous system is associated with increasing the heart rate and increasing the contractility of the heart. The disclosed system and method may be used to augment balance between the sympathetic and parasympathetic systems in AHFS patents so as to lower heart rate, elevate heart rate and/or increase heart contractility.

BRIEF DESCRIPTION OF THE DRAWINGS

FIGS. 1-4 are a sequence of drawings illustrating deployment of a first embodiment of a catheter system, in which:

FIG. 1 shows the system in a blood vessel prior to expansion of the anchoring element;

FIG. 2 is similar to FIG. 1 but shows the anchoring element expanded;

FIG. 3 illustrates the system following removal of the guide wire and dilator, and FIG. 4 is similar to FIG. 3 but shows a Swan-Ganz catheter extending through the lumen of the catheter.

DETAILED DESCRIPTION

Figure 5A:
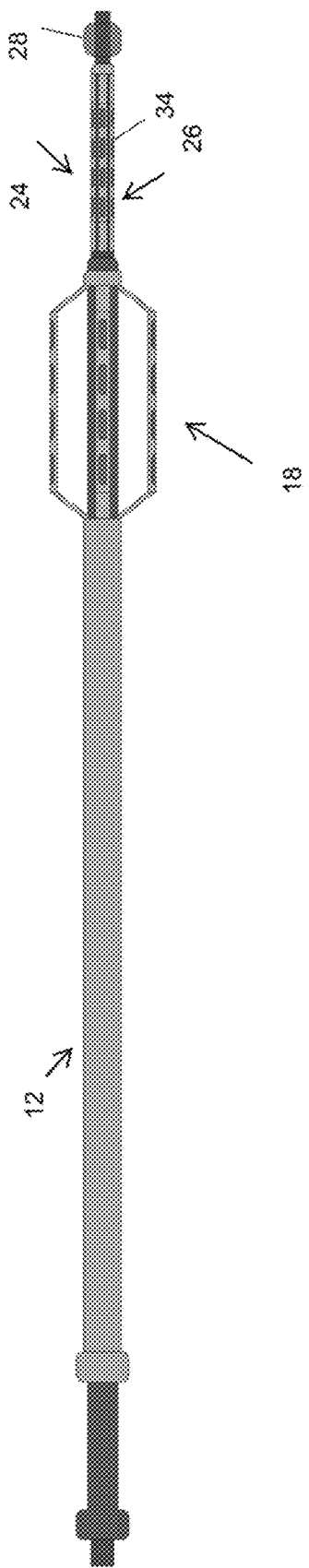
FIG. 5A is similar to FIG. 4 but shows a second neuromodulation device extending through the lumen of the catheter.

The present application discloses a catheter system for neuromodulation. One application of the system is for acute use in treating AHFS through parasympathetic and/or sympathetic neuromodulation. However it should be understood that the system may alternatively be used to treat other conditions, or to maintain autonomic balance at times where the patient's own nervous system could benefit from assistance in maintaining autonomic balance. One example of this latter application is to use the system to maintain autonomic balance while the patient is intubated, is in a coma, or is otherwise experiencing autonomic dysfunction. Other conditions that could be treated with acute neuromodulation include, but are not limited to, acute myocardial infarction, pulmonary embolism, hemorrhage, systemic inflammatory response syndrome (SIRS), sepsis, and post-surgery autonomic dysfunction.

A neuromodulation system for treating AHFS provides therapeutic elements for modulation of parasympathetic and/or sympathetic fibers. In some embodiment, only parasympathetic fibers are stimulated, while in other embodiments parasympathetic and sympathetic fibers are stimulated at the same time and/or at different times to improve autonomic balance in the heart. In preferred embodiments, the therapeutic elements are positioned on one or more catheters positioned in the vasculature of the patient and are energized to modulate nerve fibers positioned outside the vascular walls. Modulation may be carried out to activate and/or inhibit or block activation of target nerve fibers. In the disclosed system, the therapeutic elements are described as electrodes, although it is contemplated that other forms of therapeutic elements (including, but not limited to, ultrasound, thermal, or optical elements) may instead be used.

The parasympathetic and sympathetic fibers may be modulated from the same therapeutic element or element array, or from different elements or element arrays. Elements used to modulate sympathetic fibers may be positioned in the same blood vessels as those used for the parasympathetic fibers, or they may be in different blood vessels. The blood vessel and the target position of the therapeutic elements within a chosen vessel is selected based on the vessel's anatomic location relative to the target fiber so as to position the therapeutic element in close proximity to the target fiber while minimize collateral effects. For example, in the canine model, right sympathetic fibers modulating left ventricular contractility converge at the common pulmonary artery and course in the pulmonary artery nerves. Left sympathetic fibers modulating ventricular contractility are found near the common pulmonary artery, pulmonary artery nerves, and ventral lateral cardiac nerve. In contrast, sympathetic fibers controlling chronotropic and dromotropic functions are found between the superior vena cava (SVC) and aorta, between the common pulmonary artery and the proximal right pulmonary artery, between the left superior pulmonary vein and the right pulmonary artery, and elsewhere. J. L. Ardell et al, *Differential sympathetic regulation of automatic, conductile, and contractile tissue in dog heart*. The anatomy thus allows a therapeutic element to be positioned to selectively stimulate sympathetic fibers controlling ventricular inotropy to increase contractility, while avoiding chronotropic/dromotropic effects so as not to trigger tachycardia.

In human use, modulation of sympathetic fibers may be achieved using a therapeutic element positioned within the pulmonary artery so as to stimulate sympathetic fibers to increase inotropy. Moreover, therapeutic elements could additionally or alternatively be employed to stimulate parasympathetic fibers that lower heart rate. Such fibers may also be activated using intravascular electrodes located in the pulmonary arteries, although in other embodiments vagal or other parasympathetic fibers are modulated using a therapeutic element in the superior vena cava or the internal jugular vein, preferably on the right side.

In some embodiments, combined or alternating modulation of the parasympathetic and sympathetic fibers may be employed to optimize the opposing effects of parasympathetic and sympathetic modulation on heart rate—such that modulation optimizes the ability of the sympathetic system to drive the heart rate and the parasympathetic system to "apply the brakes" to slow the heart when necessary. Sensed or derived hemodynamic parameters may be used by the system to select and implement stimulation parameters, algorithms and/or to identify the therapeutic element(s) to be activated at a given time. Suitable sensed or derived hemodynamic parameters include pulmonary capillary wedge pressure (PCWP), cardiac index, derivations of vascular resistance, heart rate, and blood pressure (arterial). Other parameters may include central venous pressure, CO/CI, and cardiac filling pressures.

FIGS. 1-4 illustrate a first embodiment of a catheter system 10, which includes a treatment catheter 12, a dilator 14, and a guide wire 16. The treatment catheter 12 includes a tubular inner sheath 30 and a tubular outer sheath 32, which are connected at their distal end sections.

The distal end section of the outer sheath includes one or more anchoring elements 18 that are expanded or extended into contact with the surrounding vessel wall so as to anchor the catheter in a desired location. The anchoring element(s) may be an expandable basket or stent-like device, or one or more spline elements as illustrated in the drawings. In the illustrated configuration, these elements are outwardly expandable into contact with the vessel wall W when the outer sheath 32 is pushed distally relative to the inner sheath 30 as illustrated in FIG. 2. Since the inner and outer sheaths are connected at their distal end portions, sliding the outer sheath distally relative to the inner sheath causes the anchoring elements to bow outwardly into contact with the vessel wall as shown. Stimulation electrodes 20 are mounted to or formed on the anchoring element(s) 18, or the anchoring element(s) may themselves be configured to function as electrodes. The electrodes are preferably positioned such that expanding the anchoring elements into contact with the vessel wall places the active surfaces of the electrodes into contact with the vessel wall, allowing energy for neuromodulation to conduct from the electrodes through the vessel wall to target nerve fibers adjacent to the vessel (e.g. in the adjacent extravascular space).

The inner sheath 30 includes a lumen, allowing the catheter 12 to function both as a neuromodulation catheter and an introducer for other medical devices useful for the procedure. Examples include catheters for patient monitoring (e.g. Swan-Ganz), additional electrode catheters or leads for a variety of applications such as mapping target stimulation sites, cardiac pacing, or ablation, or catheters/leads carrying neuromodulation electrodes positionable at a second intravascular site to target additional nerve fibers.

In one method of using the first embodiment, a percutaneous Seldinger technique is used to place the guidewire 16 into the venous vasculature, such as via the femoral vein, internal or external jugular vein, or subclavian vein. The dilator 14, which is preferably preloaded into the lumen of the inner sheath 30, is advanced together with the catheter over the wire and directed to the target blood vessel. The user advances the outer sheath 32 relative to the inner sheath 30 (such as by holding the hub of the inner sheath while pushing the hub of the outer sheath distally as shown in FIG. 2)—causing the anchoring elements 18 to expand into contact with the surrounding vessel wall, thus anchoring the catheter at the target site in the vessel and placing the electrodes 20 into contact with the vessel wall. The relative positions of the inner and outer sheath hubs may be locked using a ratchet or locking mechanism (not shown) to maintain the anchoring elements in the expanded position.

The dilator and wire are removed from the catheter lumen either before or after anchoring of the catheter.

In one embodiment, the target vessel is the superior vena cava, and the catheter 12 is anchored such that energizing the electrodes (or a select group of electrodes within the array) will cause a desired effect (e.g. enhance, augment, inhibit or block signaling) on vagus nerve fibers adjacent to the superior vena cava. Once the electrodes are expanded into contact with the vessel wall, mapping procedures may be carried out as known in the art (measuring the effect of stimulus at various electrode locations) to identify the optimal positions of the electrodes or to identify the best combination of electrodes within the array to energize for the desired response.

Additional medical devices are advanced through the inner sheath lumen as discussed above, such that their distal portions extend from the distal end of the catheter. FIG. 4 shows use of a Swan-Ganz catheter 22 through the inner sheath 30. FIG. 5A shows that a second electrode lead or catheter 24 can be advanced through the lumen of the inner sheath 30. The second electrode lead or catheter may have one or more expandable anchoring elements 26 as discussed above with respect to the catheter 12 (and as shown in FIG. 5A in the unexpanded position), with electrodes 34 mounted to or formed on the anchoring elements 26 as disclosed. The second electrode lead or catheter 24 may include an inflatable balloon 28 on its distal tip as shown, to facilitate advancement of the second electrode lead/catheter 24 to a target site. It may also include sensing functionality, such as the ability to sense pressures including, but not limited to, PCWP. For example, if the second electrode lead/catheter 24 is to be positioned within the pulmonary artery, inflating the balloon within the right ventricle can help the electrode lead/catheter float with the flowing blood into the pulmonary artery in the manner similar to the way in which a Swan-Ganz catheter is positioned. The balloon 28 may be positioned on the second lead/catheter 34 itself, or on an additional catheter extending through a lumen in the lead/catheter 34.

Figure 5B:
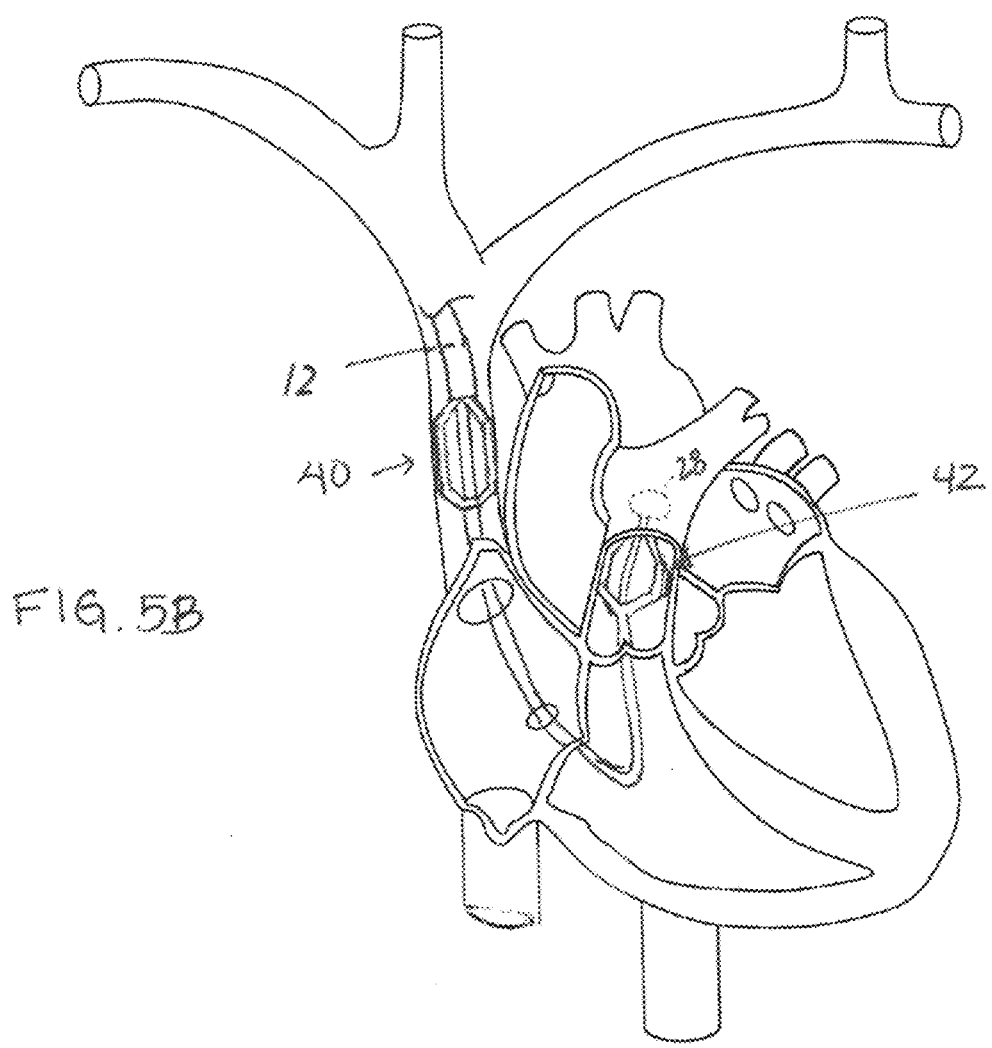
FIG. 5B schematically illustrates positioning of the neuromodulation device of FIG. 5A within the vasculature.

In one exemplary procedure using the FIG. 5A embodiment, the electrodes 20 of the catheter 12 are anchored in the superior vena cava as discussed above for neuromodulating parasympathetic activity of the vagus nerve (to slow the heart, for example), and the electrodes 34 of the second lead/catheter 24 are anchored in the pulmonary artery for directing energy to sympathetic nerves that will enhance heart contractility and/or increase heart rate. Referring to FIG. 5B, in a positioning method according to this embodiment, the catheter is advanced into the superior vena cava and anchoring elements 18 are expanded to position the electrodes 20 against the wall of the SVC, placing the first electrode array 40 in position to stimulate the vagus nerve. Next, the second lead/catheter 24 is further extended from the lumen of the inner sheath 30, and passed or caused to through the right atrium and right ventricle of the heart and into the pulmonary artery using the method described in the prior paragraph or alternative methods. Once in a target position within the pulmonary artery (e.g. pulmonary trunk, or left or right pulmonary artery), the anchoring elements of the second lead/catheter 24 are expanded, positioning the electrodes 34 in apposition with the pulmonary artery wall and thus placing the second electrode array 42 in position to stimulate sympathetic nerves (or, if desired, parasympathetic nerves) in proximity to the pulmonary artery. Pressure may be monitored using pressure transducers on the second lead/catheter, and/or the balloon may be used to monitor pulmonary capillary wedge pressure.

Figure 6:
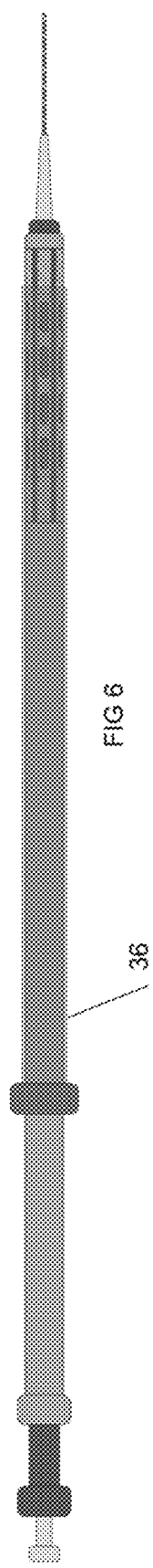
FIGS. 6 and 7 are similar to FIGS. 1 and 4 but show a second alternative configuration for expanding the anchoring element.
Figure 7:
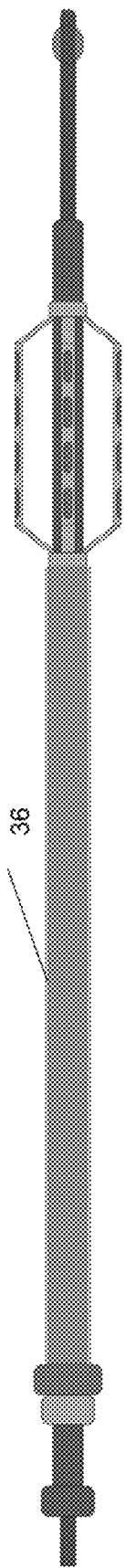

In a slightly modified version of the FIG. 1-4 embodiment, deployment of the anchoring elements 18 is accomplished by pulling the inner sheath 30 proximally relative to the outer sheath 32. FIGS. 6-7 show yet another configuration utilizing anchoring elements that are self-expandable upon retraction of an outer sleeve 36 (shown compressing the anchoring elements in FIG. 6 and withdrawn from them in FIG. 7) that maintains the anchoring element(s) in a compressed position until it is retracted. In still other embodiment, pull cables may be tensioned from the proximal end of the catheter to expand the anchoring elements.

The disclosed catheter system may be coupled to external pulse generator used to energize the electrodes using stimulation parameters selected to capture the target nerve fibers and to achieve the desired neuromodulation. Feedback to the pulse generator is provided by one or more diagnostic sensors, including feedback from sensors mounted on or extending through the lumen of the catheter-introducer. The simulation parameters may be determined or adjusted in response to information sensed by the sensors and/or derived from sensor feedback. Suitable sensed or derived hemodynamic parameters include pulmonary capillary wedge pressure (PCWP), cardiac index, derivations of vascular resistance, heart rate, blood pressure (arterial). Other parameters may include central venous pressure, CO/CI, and cardiac filling pressures.

We claim:

1. A neuromodulation system for treating a patient, comprising:
    a first therapy element adapted for positioning within a first blood vessel, the first therapy element carried on a first elongate shaft, wherein the elongate shaft of the first therapy element includes
        an outer sheath having a distal portion, and an expandable anchoring element on the distal portion, the expandable anchoring element radially expandable from the distal portion of the outer sheath from a streamlined to an expanded position in response to relative movement of a proximal portion of the outer sheath towards the distal portion, wherein the therapy element comprises electrodes on the expandable anchoring element, and
        an inner sheath slidably disposed within the outer sheath, the inner and outer sheath having distal portions fixed to one another, such that relative longitudinal movement of proximal portions of the inner and outer sheaths in opposite directions while the distal portions remain fixed to one another moves the proximal portion of the inner sheath towards the fixed distal portions to move the expandable anchoring element between streamlined and expanded positions;
    a second therapy element adapted for positioning with a second blood vessel different from the first blood vessel, the second therapy element carried on a second shaft, wherein one of the first and second shafts is slidably received within a lumen of the other of the first and second shafts; and
    a stimulator configured to (a) energize the first therapy element within the first blood vessel to deliver therapy to a first nerve fiber disposed external to the first blood vessel and (b) energize the second therapy element within the second blood vessel to deliver sympathetic therapy to a second nerve fiber disposed external to the first blood vessel.

2. The system of claim 1, further including control means for receiving input corresponding to sensed heart rate and/or blood pressure of the patient and controlling the stimulation in response to said sensed heart rate and/or blood.

3. The system of claim 1, wherein each of the first and second therapy elements is at least partially expandable to position the first and second therapy elements in contact with surrounding walls of the first and second blood vessels.

4. The system of claim 1, wherein the second therapy element is adapted for positioning within a pulmonary artery.

5. The system of claim 4, further including an expandable balloon coupled to the second therapy element, the balloon positioned such that when the first therapy element is retained in the first blood vessel, expansion of the balloon causes the second therapy element to be carried by blood flow from the heart to the pulmonary artery.

6. The system of claim 4, wherein the first therapy element is adapted for positioning within a superior vena cava.

* * * * *